United States Patent
DiBella

(10) Patent No.: US 7,069,934 B2
(45) Date of Patent: Jul. 4, 2006

(54) COMPUTER USER POSTURE DEVICE

(76) Inventor: Nicholas M DiBella, 81 Flower Dale Dr., Rochester, NY (US) 14626

( * ) Notice: Subject to any disclaimer, the term of this patent is extended or adjusted under 35 U.S.C. 154(b) by 140 days.

(21) Appl. No.: 10/692,048

(22) Filed: Oct. 23, 2003

(65) Prior Publication Data

US 2004/0079378 A1    Apr. 29, 2004

Related U.S. Application Data

(63) Continuation of application No. 10/109,789, filed on Apr. 1, 2002, now Pat. No. 6,640,809.

(60) Provisional application No. 60/278,039, filed on Mar. 23, 2001.

(51) Int. Cl.
*A61B 19/00* (2006.01)

(52) U.S. Cl. .................... 128/869; 128/878; 602/19

(58) Field of Classification Search ............... 128/859, 128/846, 877, 878, 879; 602/19–21; 70/16
See application file for complete search history.

(56) References Cited

U.S. PATENT DOCUMENTS

| | | | | |
|---|---|---|---|---|
| 1,443,009 A | * | 1/1923 | Davis | .......................... 70/226 |
| 1,956,201 A | | 4/1934 | Roberts | |
| 2,207,968 A | | 7/1940 | Brasare | |
| 3,324,851 A | | 6/1967 | Pusner | |
| 5,038,799 A | | 8/1991 | Fowler | |
| 5,086,762 A | | 2/1992 | Chee | |
| 5,732,576 A | * | 3/1998 | Moore et al. | .................. 70/16 |
| 5,746,705 A | | 5/1998 | Sheppard | |
| 6,640,809 B1 | * | 11/2003 | DiBella | ..................... 128/869 |

* cited by examiner

*Primary Examiner*—Michael A. Brown

(57) ABSTRACT

A keyboard posture device includes a lateral support shaft, left and right members, and left and right arm restraints. The frame member may be adjustably movable along the support shaft. Left and right arm restraints are also optionally adjustably movable, forward and back, on the forward struts of the left and right frame members respectively. The arm restraints extend forward from the struts and away from each other to form left and right arm crooks. The device may further includes a back pad and a wraparound strap to secure the device to the torso of the user.

16 Claims, 2 Drawing Sheets

COMPUTER USER POSTURE DEVICE

CROSS-REFERENCE TO RELATED APPLICATION

This application is a continuation of prior application Ser. No. 10/109,789 of Nicholas M DiBella filed Apr. 1, 2002, now U.S. Pat. No. 6,640,809, which claims priority from Provisional Application No. 60/278,039 filed Mar. 23, 2001.

BACKGROUND OF THE INVENTION

This invention is a posture device to encourage and/or train the user to assume proper posture for computer keyboard use, or the like.

SUMMARY OF THE INVENTION

In accordance with one aspect of the present invention there is provided a keyboard posture device having a lateral support section, left and right side strut portions extending forward from said lateral support section, and left and right arm restraints extending from said strut portions and away from each other to form left and right arm crooks in which to position the user's upper arms between elbow and bicep.

In accordance with another aspect of the present invention there is provided a keyboard posture device, including:
 a lateral support structure;
 left and right frame members each including a forward strut adjustably mounted on opposite ends of said support structure; and
 left and right arm restraints adjustably mounted on said struts of respectively said left and right frame members, said arm restraints extending away from each other to form left and right arm crooks in which to position the user's upper arms between elbow and bicep.

In accordance with yet another aspect of the present invention there is provided keyboard posture device having a lateral support structure, left and right L-shaped frame members each including a lateral crossbar and a forward strut, said crossbars slidably mounted on opposite ends of said lateral support structure, left and right arm restraints slidably mounted on said struts of said left and right frame members, respectively, and extending forward therefrom and away from each other, each forming an arm crook in which to position the user's upper arms between elbow and bicep, and a back pad mounted on said support shaft between said frame members; and means to secure said device to the torso of the user.

BRIEF DESCRIPTION OF DRAWINGS

The drawing includes FIGS. 1–4.

DETAILED DESCRIPTION

Figure 1:
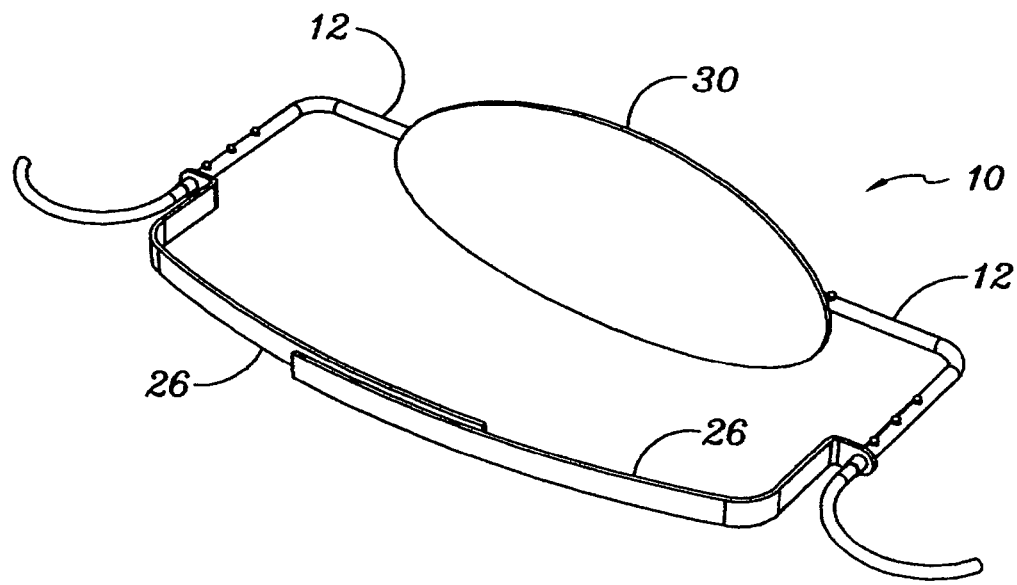
FIG. 1 is a perspective view, from above, of the posture device of this invention.
Figure 2:
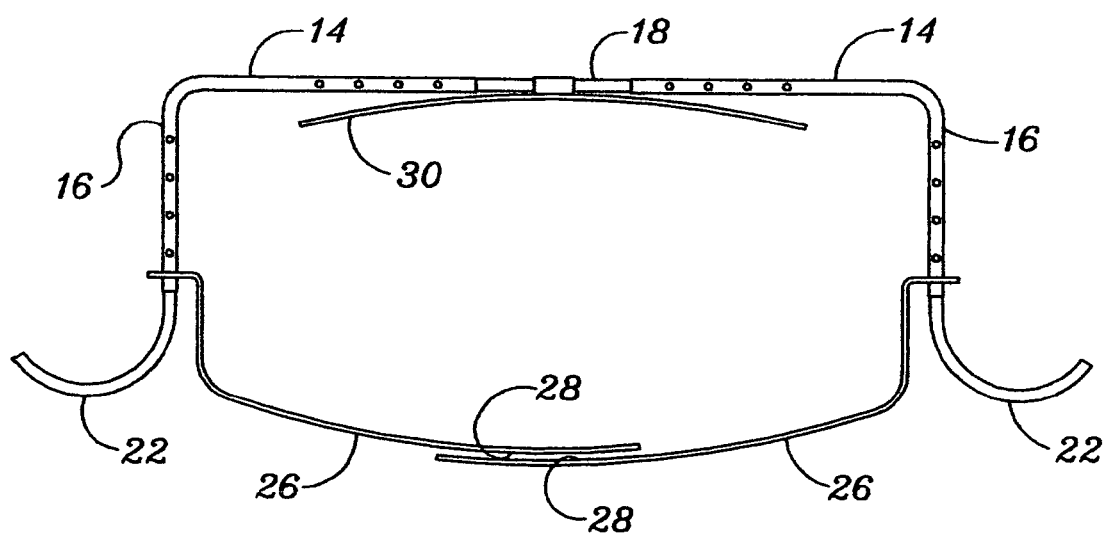
FIG. 2 is a top plan view of the posture device of FIG. 1.

Referring now to FIGS. 1 and 2, my posture device 10 includes left and right tubular frame members 12. The frame members 12 are generally L-shaped, each including a lateral crossbar portion 14 and a forward strut portion 16. The lateral crossbars 14 are slidable on opposite ends of a central lateral support shaft 18 for the purpose of adjusting the width of the device.

Figure 3:
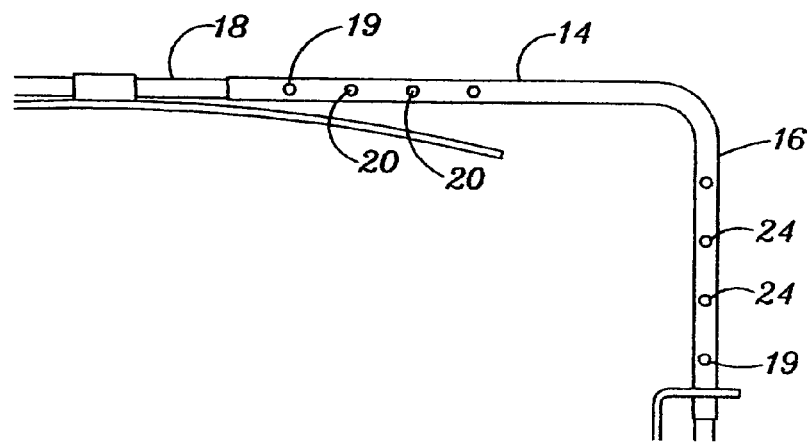
FIG. 3 is an enlarged detail view of the upper right portion of FIG. 2.

As best seen in FIG. 3, the support shaft 18 includes spring-loaded "lateral" lock buttons 19 mounted therein. Such lock buttons for length adjustment of mating tubes are well known in the art. The lateral crossbars 14 each include several holes 20 spaced therealong. Lateral adjustment of the position of each frame member 12 relative to the support shaft 18 is made by depressing the lock button 19 and sliding the frame member 12 along the support shaft until the lock button pops up in the desired hole in the frame member 12.

Left and right arm restraints 22 extend forward from the forward struts 16 of the left and right frame members 12 respectively. The arm restraints 22 are curved out and away from each other, each providing a crook in which to position the user's upper arm (between elbow and bicep). As best seen in FIG. 3, the forward struts 16 each include several holes 24 spaced therealong. The arm restraints 22 include straight portions which are slidable within their respective struts 16. The arm restraints 22 each further include a "forward" lock button 19. The arm restraints 22 are slidable relative to their respective struts 16 to adjust their forward positions, in the same manner as the width adjustment of the frame members 12.

As best shown in FIG. 1, a back pad 30 for comfort and for lumbar support is suitably mounted on the support shaft 12 between the two frame members 12. Left and right front straps 26 are connected respectively to left and right frame members 12. These straps are adapted to overlie each other in front of the user's torso. They hold the device in place on the user's person. The straps 26 include mating fastener strips 28 (such as Velcro) along their overlying portions.

Figure 4:
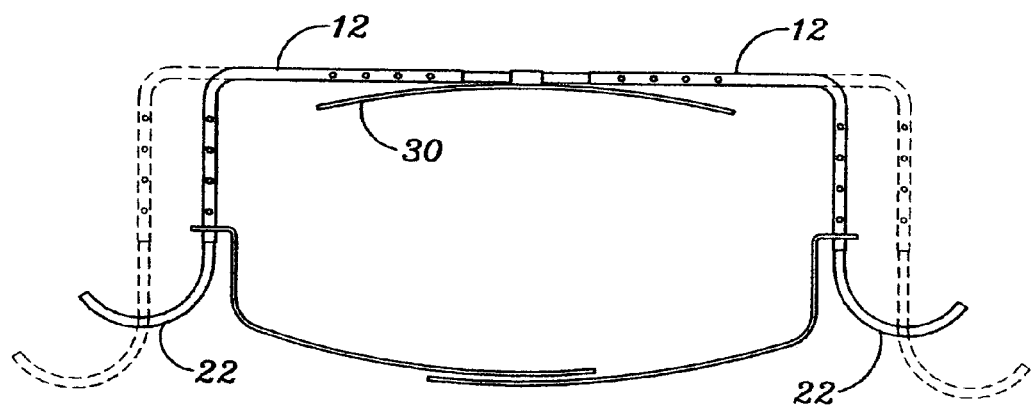
FIG. 4 is a top plan view illustrating two adjustment configurations of the device.

FIG. 4 illustrates two of the several possible size adjustments of the posture device. The smallest size adjustment is shown in solid lines. The largest size adjustment is shown in phantom lines. FIG. 4 shows the range of adjustability of my posture device. As indicated by the several holes in the crossbars 14 and struts 16, there are several possible adjustment configurations, at discrete intervals, in addition to the two that are shown.

The device is positioned for use with the crossbar 14 behind the back, and struts 16 extending forward, one on each side. The user's arms, extending down through the crooks formed by the arm restraints 22 and flexed (even slightly) at the elbows, hold the device in place. With the device in place, the user can stand or sit as desired; the device will not fall off.

Figure 5:
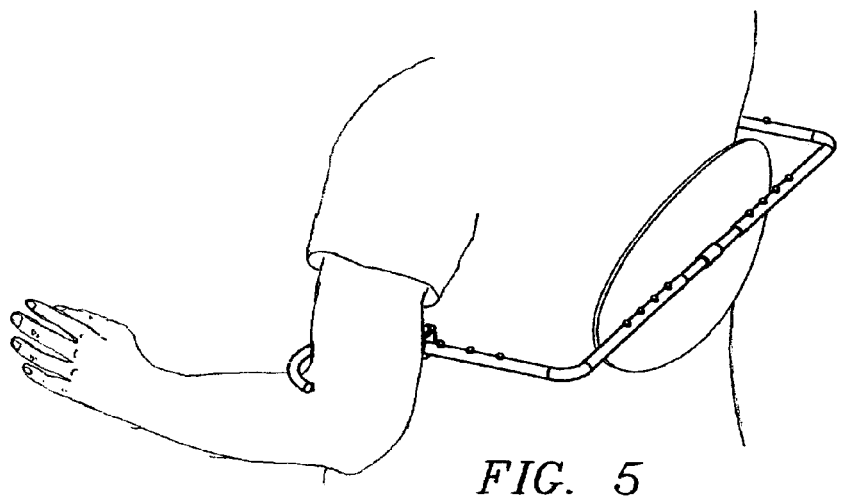
FIG. 5 shows the posture device in use.

FIG. 5 shows a user at a computer keyboard with the posture device in place on his person. If the user slumps in his chair, the device pulls arms (and hands) away from the keyboard. The only way to get hands back on the keyboard is to straighten the back. This is a very effective posture training device. It not only encourages the user to assume a proper working posture, but makes it virtually impossible to do otherwise. Additionally, I found that with the use of this device I developed better habits of posture alter only a week or two, and did not need to continue using it.

The various structural members may be rigid or resilient. Furthermore, they might have different degrees of resilience to suit the user (as do skis, for example).

The posture device described above is adjustable as to size. It is also contemplated that the frame members can be of fixed length, and be made available in different sizes to suit the user.

Any terms indicative of orientation are used with reference to drawing illustrations. Such terms are not intended as limitations but as descriptive words. Apparatus described herein retains its described character whether it be oriented as shown or otherwise.

The foregoing description of a preferred embodiment of this invention sets forth the best mode presently contemplated by the inventor of carrying out this invention. Any details as to materials, quantities, dimensions, and the like are intended as illustrative. The concept and scope of the invention are limited not by the description but only by the following claims and equivalents thereof.

What is claimed is:

1. A keyboard posture device, including:
    a rigid lateral support section;
    a back pad mounted on said rigid lateral support section at an intermediate location thereon;
    left and right side rigid strut portions extending forward from said rigid lateral support section; and
    left and right rigid arm restraints extending from said rigid strut portions and away from each other to form left and right arm crooks in which to position the user's arms between elbow and bicep.

2. A keyboard posture device as defined in claim 1, further including means to secure said device to the torso of its user.

3. A keyboard posture device as defined in claim 1, wherein said rigid lateral support section is adjustable in length.

4. A keyboard posture device as defined in claim 1, wherein said left and right side rigid strut section is adjustable in length.

5. A keyboard posture device as defined in claim 1, wherein said left and right rigid arm restraints are curved out.

6. A keyboard posture device as defined in claim 1, wherein said rigid lateral support section, said left and right side rigid side strut portions, and said left and right rigid arm restraints are of fixed length.

7. A keyboard posture device, including:
    a rigid lateral support structure;
    left and right rigid frame members each including a forward rigid strut adjustably mounted on opposite ends of said rigid support structure; and
    left and right rigid arm restraints adjustably mounted on said rigid struts of said left and right rigid frame members respectively, said right arm restraints extending away from each other to form left and right arm crooks in which to position the user's upper arms between elbow and bicep.

8. A keyboard posture device according to claim 7 further comprising a back pad mounted on said rigid support structure between said rigid struts; and
    means to secure said device to the torso of the user.

9. A keyboard posture device as defined in claim 7 wherein said rigid lateral support structure is adjustable in length.

10. A keyboard posture device as defined in claim 7 wherein said left and right side rigid strut portions are adjustable in length.

11. A keyboard posture device as defined in claim 7 wherein said left and right rigid arm restraints are curved out.

12. A keyboard posture device according to claim 7 wherein said rigid lateral support section, and said left and right side rigid strut portions, and said left and right rigid arm restraints are of fixed length.

13. A keyboard posture device, including:
    a lateral support structure;
    left and right L-shaped rigid frame members each including a rigid lateral crossbar and a rigid forward strut, said rigid crossbars slidably mounted on opposite ends of said rigid lateral support structure;
    left and right arm rigid restraints slidably mounted on said rigid struts of said left and right rigid frame members, respectively, and extending forward therefrom and away from each other, each forming an arm crook in which to position the user's upper arms between elbow and bicep; and
    a back pad mounted on said support structure between said left and right rigid frame members; and means to secure said device to the torso of the user.

14. A keyboard posture device as defined in claim 13 wherein said support structure includes left and right lateral lock buttons thereon, said left and right crossbars each including holes spaced therealong for selective insertion among them of said left and right lock buttons, respectively.

15. A posture device as defined in claim 13 wherein said left and right arm restraints including left and right forward lock buttons thereon and said left and right struts each including holes spaced therealong for selective insertion among them of said left and right forward lock buttons, respectively.

16. A keyboard posture device, including:
    a lateral support section having left and right buttons thereon;
    left and right side strut portions extending from said lateral support sections wherein said left and right struts are adjustable in length, said left and right rigid strut portions each including holes spaced therealong for selecting insertion among them of said left and right lock buttons, respectively; and
    left and right rigid arm restraints extending from said strut portions and away from each other to form left and right arm crooks in which to position the user' arm between elbow and bicep.

* * * * *